United States Patent [19]

Sims

[11] E Patent Number: Re. 33,727

[45] Reissued Date of Patent: Oct. 29, 1991

[54] BANDAGE FRAME

[75] Inventor: Larry A. Sims, Hermosa Beach, Calif.

[73] Assignee: Baxter International, Inc., Deerfield, Ill.

[21] Appl. No.: 548,186

[22] Filed: Nov. 2, 1983

Related U.S. Patent Documents

Reissue of:

[64] Patent No.: 4,372,303
Issued: Feb. 8, 1983
Appl. No.: 186,351
Filed: Sep. 11, 1980

[51] Int. Cl.[5] ..... A61B 19/08

[52] U.S. Cl. ..... 128/85 L

[58] Field of Search ..... 128/82, 846, 849–854, 128/887, 888, 155–157

[56] References Cited

U.S. PATENT DOCUMENTS

| | | | |
|---|---|---|---|
| Re. 24,906 | 12/1960 | Ulrich | 206/59 |
| Re. 31,886 | 5/1985 | Hodgson | 428/40 |
| Re. 31,887 | 5/1985 | Hodgson | 428/355 |
| 2,591,779 | 4/1952 | Buck | 154/95 |
| 2,626,226 | 1/1953 | Adair | 154/95 |
| 2,703,083 | 3/1955 | Gross | 128/156 |
| 2,752,038 | 6/1952 | Abbott | 206/63.2 |
| 2,783,172 | 2/1957 | Avery | 154/46.8 |
| 2,884,126 | 4/1959 | Ulrich | 206/59 |
| 2,924,331 | 2/1960 | Hoey | 206/63.2 |
| 2,927,689 | 3/1960 | Look | 206/63.2 |
| 3,007,571 | 11/1961 | Marinaro | 206/63.2 |
| 3,065,120 | 11/1962 | Avelar | 154/46.8 |
| 3,194,717 | 7/1965 | Albert . | |
| 3,236,370 | 2/1966 | Pereny et al. | 206/63.2 |
| 3,246,049 | 4/1966 | Webber | 260/829 |
| 3,260,260 | 7/1966 | Questel | 128/132 |
| 3,288,135 | 11/1966 | Pereny et al. | 128/132 |
| 3,299,890 | 1/1967 | Parker | 128/156 |
| 3,311,338 | 3/1967 | Culley | 248/205 |
| 3,315,677 | 4/1967 | Tyrrel, Jr. | 128/288 |
| 3,349,765 | 10/1967 | Blanford | 128/132 |
| 3,364,928 | 1/1968 | Creager, Jr. et al. | 128/132 |
| 3,373,741 | 3/1968 | Hill et al. | 128/90 |
| 3,389,827 | 6/1968 | Abere et al. | 220/53 |
| 3,416,520 | 12/1968 | Creager, Jr. | 125/132 |
| 3,416,524 | 12/1968 | Meier | 128/156 |
| 3,423,277 | 1/1969 | Dipner | 161/118 |
| 3,452,750 | 7/1969 | Blanford | 128/132 |
| 3,483,018 | 12/1969 | Waldman | 117/68.5 |
| 3,490,971 | 1/1970 | Walters | 156/79 |
| 3,520,306 | 7/1970 | Gardner et al. | 128/335 |
| 3,645,835 | 2/1972 | Hodgson | 161/146 |
| 3,675,844 | 7/1972 | Sorrell | 229/80 |
| 3,679,458 | 7/1972 | Sorrell, et al. | 117/68.5 |
| 3,774,592 | 11/1973 | Lahr | 128/2.1 E |
| 3,852,823 | 12/1974 | Jones | 2/68 |
| 3,857,140 | 12/1974 | Leveen | 24/87 TB |
| 3,861,008 | 1/1975 | Wannag | 24/255 P |
| 3,870,593 | 3/1975 | Elton et al. | 161/159 |
| 3,878,843 | 4/1975 | Morgan | 128/132 D |
| 3,889,667 | 6/1975 | Collins | 128/132 D |
| 3,896,789 | 7/1975 | Trancik | 128/2 R |
| 3,900,617 | 8/1975 | Grenoble | 427/387 |

(List continued on next page.)

FOREIGN PATENT DOCUMENTS

| | | |
|---|---|---|
| 1935916 | 2/1971 | Fed. Rep. of Germany . |
| 842617 | 7/1960 | United Kingdom . |
| 1494643 | 12/1977 | United Kingdom . |
| 1502628 | 3/1978 | United Kingdom . |
| 1509447 | 5/1978 | United Kingdom . |

*Primary Examiner*—C. Fred Rosenbaum
*Assistant Examiner*—Anthony M. Gutowski
*Attorney, Agent, or Firm*—Willian Brinks Olds Hofer Gilson & Lione

[57] ABSTRACT

A frame for spreading relatively large adhesive backed bandages into a generally flat configuration for applying to a patient. Such bandages might be for a wound dressing, burn dressing, surgical incise drape, etc. The frame is attached to the bandage when the bandage is being stuck to the patient, but the frame is removed so as not to interfere with subsequent movement of the patient's anatomy.

4 Claims, 1 Drawing Sheet

U.S. PATENT DOCUMENTS

| | | | |
|---|---|---|---|
| 3,916,887 | 11/1975 | Kelly | 128/132 |
| 3,973,563 | 8/1976 | Green et al. | 128/156 |
| 4,005,247 | 1/1977 | Graham | 526/15 |
| 4,024,312 | 5/1977 | Korpman | 428/343 |
| 4,028,474 | 6/1977 | Martin | 428/40 |
| 4,067,327 | 1/1978 | Shannon, Sr. | 128/132 D |
| 4,082,705 | 4/1978 | Beede et al. | 260/4 R |
| 4,097,943 | 7/1978 | O'Connell | 5/335 |
| 4,112,177 | 9/1978 | Salditt et al. | 428/304 |
| 4,112,213 | 9/1978 | Waldman | 526/279 |
| 4,157,410 | 6/1979 | McClintock | 428/40 |
| 4,162,356 | 7/1979 | Grenoble | 528/31 |
| 4,163,077 | 7/1979 | Antonsen et al. | 128/355 |
| 4,182,449 | 1/1980 | Kozlow | 206/441 |
| 4,182,789 | 1/1980 | Castelluzzo | 428/40 |
| 4,201,808 | 5/1980 | Cully et al. | 428/40 |
| 4,202,292 | 5/1980 | Daoroski | 428/219 |
| 4,219,596 | 8/1980 | Takemoto et al. | 428/41 |
| 4,253,899 | 3/1981 | Takemoto et al. | 156/277 |
| 4,263,906 | 4/1981 | Finley | 128/157 |
| 4,394,904 | 7/1983 | Larimore | 206/447 |

BANDAGE FRAME

Matter enclosed in heavy brackets [ ] appears in the original patent but forms no part of this reissue specification; matter printed in italics indicates the additions made by reissue.

BACKGROUND

In a co-pending, co-owned application invented by Frederic Grossmann and Larry A. Sims, filed Sept. 11, 1980, Ser. No. 186,352, *now U.S. Pat. No. 4,374,520,* clamp on and other type of handles are described for use in applying large area adhesive backed bandages to patients. Such bandages when applied to a patient require extremely careful handling, as shown in U.S. Pat. No. 3,236,370, to prevent the bandage from sticking from itself or excessively wrinkling. When used as an "incise" drape, a surgical incision is made directly through the bandage and into the patient.

SUMMARY OF THE INVENTION

The problem of handling large area bandages, such as for burn dressings, wound dressings, and incise drapes, is overcome by the present invention which includes a frame structure for spreading the highly flexible adhesive backed bandage into a somewhat flattened configuration during the application of such bandage to a patient. After the bandage has been applied, the frame structure is removed from the bandage, permitting the bandage to have full flexible freedom to move with the patient's body.

THE DRAWINGS

DETAILED DESCRIPTION

Figure 1:
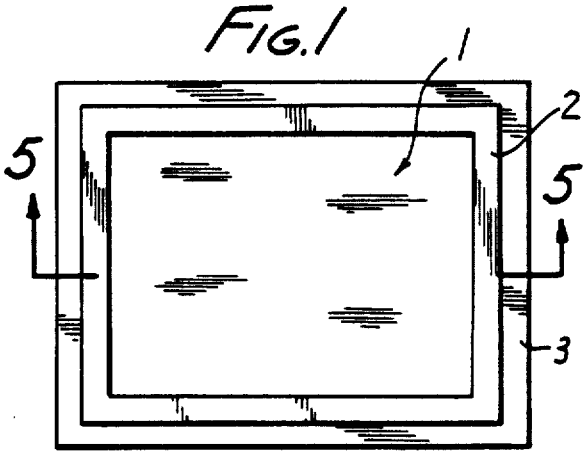
FIG. 1 is a top plan view of the frame attached to the adhesive backed bandage.
Figure 2:
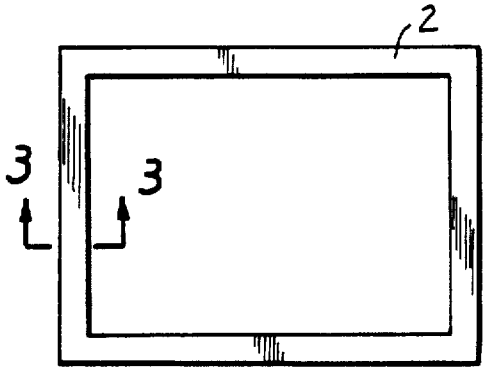
FIG. 2 is a top plan view of the frame prior to attaching to such bandage.

In FIG. 1, an adhesive backed flexible bandage, shown generally at 1, is secured to a frame 2. For easy attachment and detachment of the frame, a protruding border 3 of the flexible drape is provided. The frame unattached to flexible bandage 1 is shown in FIG. 2.

Figure 3:
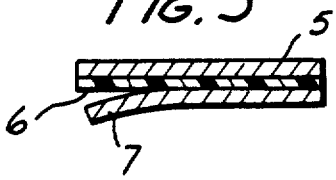
FIG. 3 is an enlarged sectional view taken along line 3—3 showing a first embodiment of the frame in relatively thin configuration.
Figure 4:
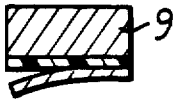
FIG. 4 is a sectional view similar to FIG. 3, but showing a second embodiment of the frame construction of a thicker configuration.

In a first embodiment of the frame shown in the sectional view of FIG. 3, a frame back 5 is coated with an adhesive 6, which in turn is protected by a peel off liner 7. In this figure, the frame back 5 is of relatively thin material, such as a heavy paper. Thermoplastic or other material could also be used for the frame back. FIG. 4 shows a second embodiment of the frame wherein a frame back 9 is of a relatively thicker material, but not as wide as the FIG. 3 embodiment.

Figure 5:
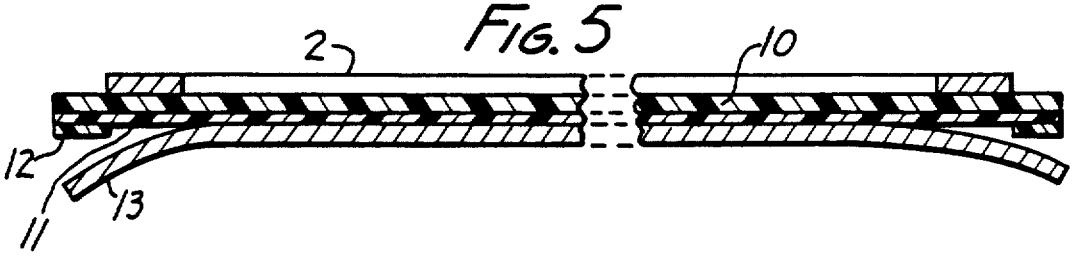
FIG. 5 is an enlarged sectional view taken along line 5—5 of FIG. 1.

When the frame 2 is attached by its adhesives to the top of flexible bandage 1, the configuration is that of the sectional view of FIG. 5. Bandage 1 preferably has a backing 10 that is coated with an adhesive 11. A strip member 12 secured to adhesive 11 prevents the removable liner 13 from sticking to an edge portion of the flexible bandage. This provides an easily graspable tab on liner 13 that is unstuck to the adhesive when peeling off the liner 13. Liner 13 can be of a discardable paper material. The flexible backing 10 and adhesive 11 are preferably of a water vapor permeable, liquid water and bacteria impermeable film material. One type of such water vapor permeable bandage is manufactured by the British firm of Smith & Nephew and marketed in the United States under the trademark OP-SITE. An instruction sheet for such OP-SITE bandage is attached showing how it is applied to a patient without the benefit of the present invention.

Figure 6:
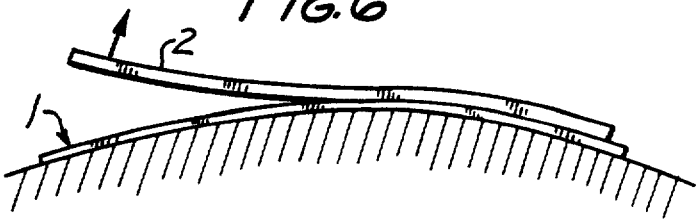
FIG. 6 is a side elevational view showing the frame being peeled from the bandage after application to a patient.

When the frame 2 and flexible bandage 1 are attached to each other and liner 13 has been removed, the bandage is smoothed down against the contours of a patient's anatomy. Preferably, the frame 2 is slightly flexible or bendable so as to temporarily conform to a patient's anatomy during application of the flexible bandage. After such application, the frame can be peeled off of the flexible bandage 1, as shown in FIG. 6. Thus, after application, the bandage resumes its very highly flexible nature so as to readily move with the patient's body. Even though, as shown in FIG. 6, the frame is slightly flexible or bendable, it still remains stiffer than the flexible bandage material itself.

Figure 7:
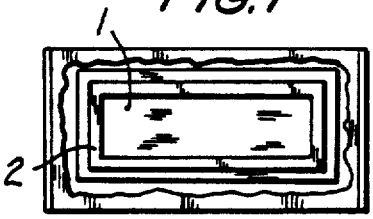
FIG. 7 is a top plan view of a sterile package broken away to show a package frame and bandage system.
Figure 8:
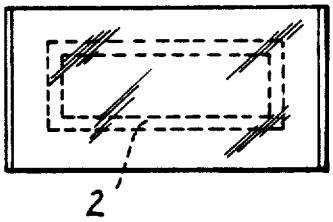
FIG. 8 is a sterile containing a frame only.

The system, which includes the frame 2 and flexible bandage 1, are contained within a sterile package, as shown in FIG. 7. The package of FIG. 7 has been broken away to reveal the frame and bandage. In FIG. 7, the frame can be preattached to the bandage, or alternatively, they can be attached to each other upon opening the package of FIG. 7. FIG. 8 shows a sterile package in which only the frame is within the package.

Throughout the specification and claims, the term "bandage" has been used in a very broad sense to include any large area adhesive backed sheet material applied to a patient, such as a wound dressing, burn dressing, incise drape, etc. The term "frame" has also been used in a broad sense to include an attachable structure which is applied to the drape for spreading into a more manageable configuration during the application to the patient. Such frame need not enclose a central opening nor be rectangular in shape.

In the foregoing description, specific examples have been used to describe the invention. However, it is understood by those skilled in the art that certain modifications can be made to these examples without departing from the spirit and scope of the invention.

[We] *I* claim:

[1. A system for bandaging a patient comprising:

a flexible bandage having a backing with an adhesive on a surface thereof for applying to a patient; and a frame means which is substantially less flexible than the bandage and is attachable to the backing thereof for maintaining said bandage in a generally flat configuration and for controlling wrinkling during handling and application of the bandage to the patient when attached thereto;

whereby the bandage may resume its flexible nature after application to the patient and removal of the frame means, so as not to interfere with the flexible functioning of the bandage on the patient's anatomy.]

[2. A system for bandaging a patient as set forth in claim 1, wherein the frame means is stiffer than the bandage.]

[3. A system for bandaging a patient as set forth in claim 2, wherein the frame means is heavy paper.]

[4. A system for bandaging a patient as set forth in claim 2, wherein the frame means is thermoplastic.]

[5. A system for bandaging a patient as set forth in claim 1, 2, 3 or 4 wherein the flexible bandage is a dressing for a wound.]

[6. A system for bandaging a patient as set forth in claim 2, wherein the flexible bandage is a burn dressing.]

[7. A system for bandaging a patient as set forth in claim 1, 2, 3 or 4 wherein the flexible bandage is a surgical drape.]

[8. A system for bandaging a patient as set forth in claim 4, wherein the flexible bandage is an incise surgical drape and is severable at a surgical incision.]

[9. A system for bandaging a patient as set forth in claim 1, 2, 3 or 4 wherein the bandage is permeable to water vapor, but impermeable to liquid water and bacteria.]

[10. A system for bandaging a patient as set forth in claim 1, 2, 3 or 4 wherein the backing and adhesive are transparent for viewing a patient beneath the bandage.]

[11. A system for bandaging a patient as set forth in claim 1, 2, 3 or 4 wherein the adhesive forms a continuous coating on the backing so that the adhesive is adapted to secure the backing directly to the wound or incision area.]

[12. A system for bandaging a patient as set forth in claim 1, 2, 3 or 4 wherein the frame is secured to the bandage by an adhesive.]

[13. A system for bandaging a patient as set forth in claim 1, 2, 3 or 4 wherein the frame is bendable.]

[14. A system for bandaging a patient as set forth in claim 1, 2, 3 or 4 wherein the frame is preattached to the bandage, and both the frame and flexible bandage are sterile and inside a sterility protecting package.]

[15. A system for bandaging a patient as set forth in claim 1, 2, 3 or 4 wherein the bandage has a removable liner protecting the adhesive prior to use.]

[16. In a flexible bandage or wound dressing having a backing with an adhesive on one side thereof for applying to a patent, the improvement comprising:

a reversibly attachable frame means;

said frame being substantially less flexible than the bandage or wound dressing and attachable to the backing thereof for maintaining said bandage or wound dressing in a generally flat configuration and having external dimensions sufficient to control wrinkling across a major area of the flexible bandage when attached thereto during application;

whereby the bandage or wound dressing may resume its flexible nature after application to the patient and removal of the frame means, so as not to interfere with the flexible functioning of the bandage or dressing on the patient's anatomy.]

17. [A frame as set forth in claim 16,] *In a flexible bandage or wound dressing having a backing with an adhesive covering one surface thereof so that the bandaging area of the flexible bandage can be directly adhered to a patient, and a removable liner protecting the adhesive prior to use, the improvement comprising:*

*a frame means which can be attached to and detached from said bandage;*

*said frame being bendable so as to temporarily conform to a patient's anatomy during application of the flexible bandage, said frame being substantially less flexible than the bandage or wound dressing for maintaining said bandage or wound dressing in a generally flat configuration, and said frame having external dimensions sufficient to control wrinkling across a major area of the flexible bandage when attached thereto during application;*

*whereby the bandage or wound dressing may resume its flexible nature after application to the patient and removal of the frame means, so as not to interfere with the flexible functioning of the bandage or wound dressing on the patient's anatomy,* wherein the frame is generally rectangular with an open central portion.

[18. A frame as set forth in claim 16, wherein the frame is sterile and in a sterility protecting package.]

[19. A frame as set forth in claim 17, wherein the frame is bendable, but is stiffer than the bandage.]

[20. A method of bandaging a patient with a flexible bandage comprising the steps of:

(a) securing to the bandage a frame means that is substantially less flexible than the bandage for maintaining said bandage in a generally flat configuration and for controlling wrinkling during handling and application of the bandage to the patient;

(b) applying the bandage to a patient while the frame means is secured to the bandage; and (c) separating the frame means from the bandage so the frame means does not interfere with the flexible functioning of the bandage of such patient's anatomy.]

[21. A method of bandaging a patient as set forth in claim 20, wherein the securing step includes adhesively attaching such frame to the bandage.]

[22. A method of bandaging a patient as set forth in claim 20, wherein the separating step includes breaking apart an adhesive joint between the frame and the handle.]

[23. A method of bandaging a patient as set forth in claim 22, wherein the breaking apart of the adhesive joint includes progressively peeling the bandage and frame apart.]

[24. A method of bandaging a patient with a flexible bandage comprising the steps of:

(a) securing to the bandage a frame means that is substantially less flexible than the bandage for maintaining said bandage in a generally flat configuration and for controlling wrinkling during handling and application of the bandage to the patient; said frame means being manually bendable to temporarily conform to an area of the patient's anatomy;

(b) applying the bandage to a patient while the frame means is secured to the bandage with the bandage being applied during a bending action of the frame means about the patient's anatomy; and (c) separating the frame means from the bandage to provide increased flexibility of the bandage on such patient's anatomy.]

[25. A system for bandaging a patient comprising:

a flexible bandage having a transparent backing that is permeable to water vapor, but impermeable to liquid water and bacteria;

a transparent flexible adhesive continuously covering one surface of the backing so that the entire bandaging area of the flexible bandage can be directly adhered to a patient;

a removal liner associated with said adhesive for protecting the adhesive prior to use; and a frame means which is substantially less flexible than the bandage and is attachable to the backing thereof for maintaining said bandage in a generally flat configuration and for controlling wrinkling during handling and application of the bandage to the patient when attached thereto;

whereby the bandage may resume its flexible nature after application to the patient and removal of the frame means, so as not to interfere with the flexible functioning of the bandage on the patient's anatomy.]

[26. A system for bandaging a patient as set forth in claim 25, wherein the frame means is stiffer than the bandage.]

[27. A system for bandaging a patient as set forth in claim 26, wherein the frame means is heavy paper.]

[28. A system for bandaging a patient as set forth in claim 26, wherein the frame means is thermoplastic.]

*29. A system for bandaging a patient comprising:*

*a flexible bandage having a backing with an adhesive covering one surface thereof so that the bandaging area of the flexible bandage can be directly adhered to a patient;*

*a removable liner for protecting the adhesive prior to use; and*

*a bendable frame means which is substantially less flexible than the bandage and is removably attached to the backing opposite the surface covered with adhesive for maintaining said bandage in a generally flat configuration, said frame means having external dimensions sufficient to control wrinkling across a major area of the flexible bandage during handling and application of the bandage to the patient;*

*whereby the bandage may resume its flexible nature after application to the patient and removal of the frame means, so as not to interfere with the flexible functioning of the bandage on the patient's anatomy,*

*wherein the frame is generally rectangular with an open central portion.*

*30. A system for bandaging a patient comprising:* a flexible bandage having a transparent backing that is permeable to water vapor, but impermeable to liquid water and bacteria;

a transparent flexible adhesive continuously covering one surface of the backing so that the entire bandaging area of the flexible bandage can be directly adhered to a patient;

*a removable liner associated with said adhesive for protecting the adhesive prior to use; and*

*a frame means which is substantially less flexible than the bandage and is attachable to the backing thereof for maintaining said bandage in a generally flat configuration and for controlling wrinkling during handling and application of the bandage to the patient when attached thereto;*

*whereby the bandage may resume its flexible nature after application to the patient and removal of the frame means, so as not to interfere with the flexible functioning of the bandage on the patient's anatomy,*

*wherein the frame is generally rectangular with an open central position.*

*31. A system for bandaging a patient comprising:*

*a flexible bandage having a backing that is permeable to water vapor, but impermeable to liquid water and bacteria;*

*a flexible adhesive continuously covering one surface of the backing so that the bandaging area of the flexible bandage can be directly adhered to a patient, wherein said adhesive is permeable to water vapor, but impermeable to liquid water and bacteria;*

*a removable liner associated with said adhesive for protecting the adhesive prior to use; and*

*a frame means removably secured to the surface of the backing opposite the surface covered with adhesive;*

*wherein said frame means is substantially less flexible than the bandage but is bendable so as to temporarily conform to a patient's anatomy during application of the flexible bandage, and has external dimensions sufficient to maintain said bandage in a generally flat configuration and for controlling wrinkling across a major area of the flexible bandage during handling and application to a patient,*

*wherein the frame is generally rectangular with an open central portion.*

* * * * *